US006887814B2

(12) United States Patent
Herbst et al.

(10) Patent No.: US 6,887,814 B2
(45) Date of Patent: May 3, 2005

(54) PROCESS FOR THE IMMOBILIZATION OF A HOMOGENEOUS CATALYST, AND CATALYTIC MATERIAL

(75) Inventors: Konrad Herbst, Søborg (DK); Michael Brorson, Holte (DK); Iver Schmidt, Copenhagen Ø (DK); Claus J. H. Jacobsen, Jægerspris (DK)

(73) Assignee: Haldor Topsoe A/S, Lyngby (DK)

( * ) Notice: Subject to any disclaimer, the term of this patent is extended or adjusted under 35 U.S.C. 154(b) by 71 days.

(21) Appl. No.: 10/338,653

(22) Filed: Jan. 9, 2003

(65) Prior Publication Data

US 2003/0139283 A1 Jul. 24, 2003

(30) Foreign Application Priority Data

Jan. 24, 2002 (DK) ........................................ 2002 00127

(51) Int. Cl.⁷ ................................................ B01J 29/06
(52) U.S. Cl. ............................. 502/64; 502/60; 502/71; 502/77
(58) Field of Search ............................. 502/60, 64, 71, 502/77

(56) References Cited

U.S. PATENT DOCUMENTS

| | | | |
|---|---|---|---|
| 4,508,842 A | | 4/1985 | Onuma et al. |
| 5,723,397 A | | 3/1998 | Verduijn |
| 5,849,258 A | | 12/1998 | Lujano et al. |
| 5,990,039 A | * | 11/1999 | Paul et al. .................... 502/326 |
| 6,087,513 A | * | 7/2000 | Liao et al. .................... 549/524 |
| 6,241,960 B1 | | 6/2001 | Topsoe et al. |
| 6,287,645 B1 | * | 9/2001 | Balkus et al. ................ 427/597 |
| 6,565,826 B2 | | 5/2003 | Jacobsen et al. |
| 2001/0031241 A1 | | 10/2001 | Lacombe et al. |
| 2002/0034471 A1 | | 3/2002 | Jacobsen et al. |
| 2002/0183577 A1 | * | 12/2002 | Haw et al. .................... 585/639 |
| 2002/0192155 A1 | | 12/2002 | Sterte et al. |
| 2003/0008770 A1 | * | 1/2003 | Srinivas et al. .............. 502/124 |

FOREIGN PATENT DOCUMENTS

| | | |
|---|---|---|
| DE | 19913395 | 9/2000 |
| DE | 19913396 | 9/2000 |
| EP | 0695215 Ba | 10/1997 |
| EP | 1002764 A1 | 5/2000 |
| WO | WO 95/29751 A | 11/1995 |
| WO | WO 97/47381 A | 12/1997 |
| WO | WO-00/00287 A | 1/2000 |

OTHER PUBLICATIONS

C.J.H. Jacobsen et al., "Mesoporous Zeolite Single Crystals", *J. Am. Chem. Soc.*, vol. 122, 2000, pp. 7116–7117.
B.T. Holland et al., "Dual Templating of Macroporous Silicates with Zeolite Microporous Frameworks", *J. Am. Chem. Soc.* vol. 121, 1999, pp. 4308–4309.
Claus Madsen et al., "Nanosized Zeolite Crystals—Convenient Control of Crystal Size Distribution by Confined Space Synthesis," *Chem. Comm.*, 1999, pp. 673–674.
J.S. Beck et al., "A New Family of Mesoporous Molecular Sieves Prepared With Liquid Crystal Templates", *Journal of the American Chemical Society*, vol. 114, Dec. 30, 1992, pp. 10834–10843.
Carmen Schuster et al., "Modification of Faujasites to Generate Novel Hosts for Ship–in–a–Bottle Complexes", *Catalysis Today*, vol. 60, No. 3, Jul. 25, 2000, pp. 193–207.
C. Heinrichs et al., "Novel Zeolite Hosts For Ship–in–a–Bottle Catalysts", *Catalysis Letters*, vol. 58, No. 2/3, Apr. 1999, pp. 75–80.
C.J. Jacobsen et al., "Mesoporous Zeolite Single Crystals", *Journal of the American Chemical Society*, vol. 122, 2000, pp. 7116–7117, 2000.
C.J.H. Jacobsen et al., "Mesoporous Zeolites", *Studies in Surface Science and Catalysis*, vol. 135, 2001, pp. 167–174.
S.A. Chavan et al., "Selective Oxidation of Para–Xylene to Terephthalic Acid by Mu3–Oxo–Bridged Co/Mn Cluster Complexes Encapsulated in Zeolite–Y", *Journal of Catalysis*, vol. 204, No. 2, Dec. 10, 2001, pp. 409–419.
C.R. Jacobsen et al., "Selective Oxidation Over Copper and Manganese Salens Encapsulated in Zeolites", *Microporous and Mesoporous Materials*, vol. 22, No. 1–3, Jun. 17, 1998, pp. 465–474.

* cited by examiner

*Primary Examiner*—Christina Johnson
(74) *Attorney, Agent, or Firm*—Dickstein Shapiro Morin & Oshinsky LLP

(57) ABSTRACT

The invention concerns a process for the immobilization of a homogeneous catalyst comprising immobilizing the homogeneous catalyst in zeotype crystals with a non-crystallographic mesopore system and a mesopore volume of the zeotype crystals above 0.25 ml/g. The invention also concerns a catalytic material prepared by the immobilization process.

7 Claims, No Drawings

PROCESS FOR THE IMMOBILIZATION OF A HOMOGENEOUS CATALYST, AND CATALYTIC MATERIAL

This invention relates to the application of zeolite crystals as hosts for homogeneous catalysts, the so-called "ship-in-the-bottle" catalysts, and it concerns a catalytic material and a process for its preparation.

In the present invention the zeolite host is a mesoporous zeolite, in which the structural modifications of the zeolite morphology leading to mesoporosity is primarily introduced into the individual zeolite single crystals during zeolite crystallization and not by post-treatments of a conventionally crystallised zeolite material.

For many transformations of organic functional groups, homogeneous catalysts have been developed with a high activity and selectivity. Homogeneous catalytic reactions are usually carried out under mild reaction conditions in an appropriate solvent, where not only the starting materials and a metal catalyst, but also the reaction products are dissolved. From these complex mixtures it is often difficult to isolate the reaction product or to separate the catalyst for a repeated use. For this reason efforts are made to combine homogeneous catalysis with the advantages of heterogeneous catalysis, where catalyst separation, e.g. from a liquid phase, can be achieved by simple filtration.

This combination can be achieved by immobilisation of catalytically active metal complexes on an appropriate inert support material. Various methods for the immobilisation of catalytically active metal complexes have been described in the literature e.g. grafting, physical adsorption, ion-pair formation, and entrapment. These are described in D. E. De Vos, I. F. J. Vankelecom, P. A. Jacobs (Eds.), Chiral Catalyst Immobilisation and Recycling, Wiley-VCH, Weinheim, Germany, 2000, incorporated herein by reference. Many of these methods include small chemical modifications of the active metal complexes in order to anchor the molecules on the carrier surface, which usually influences the catalytic performance in a negative way.

One approach to immobilising unmodified metal complexes is to encapsulate them inside the pore system of an inorganic porous support material. Appropriate materials for this purpose are zeolites with a system of micropores of crystallographically defined size and a channel system connecting the pores. For some zeolites, cage-structures are also a constituent of the micropore system. By a stepwise introduction of ligand parts into the pore system it is possible to synthesise metal complexes inside the micropores which are larger than the channel system (the so-called "ship-in-a-bottle" synthesis). In such systems the homogeneous catalyst is called the "guest" and the zeolite support is called the "host".

Inside the micropores, the metal complex can react with organic molecules capable of passing through the channel system of the carrier. Since the metal complex is larger than the channel diameter, leaching of the metal complex into solution can be almost completely avoided. The preparation of such "ship-in-a-bottle" catalysts has been described in DE Patent Applications Nos. 19913395 and 19913396. The applications describe the synthesis of various compounds in the mesopores of a zeolite, the mesopores being enclosed exclusively by micropores. However, the use of conventional zeolites as support materials for "ship-in-a-bottle" catalysts is limited since many of the catalytically active metal complexes are larger than the zeolite micropores. Treatment of Al-containing zeolites by steam or mineral acids leads to zeolite dealumination and the formation of mesopores large enough for the encapsulation of many catalytically active metal complexes. However, this dealumination procedure is connected with a considerable experimental effort.

Furthermore, since the homogeneous catalyst in "ship-in-the-bottle" catalysts is located in the pore system of the host material it partially blocks the micropores and thereby limits mass-transport to and from the active sites. Occasionally, the guest molecules will also be located far from the surface of the host crystal and this can also infer a mass-transport limitation of the reaction rate.

Consequently, it is desirable to maximise the amount of guest molecules accessible at the external surface of the host material. At the same time, it is desirable to maximise the external surface area of the host material. In principle, this could be achieved by using very small, nanosized host crystals having a crystal size between 0.1 nm and 100 nm. However, using such small crystals would prevent or severely limit the possibilities for separating the catalyst from the reaction mixture by a filtration. Also, very small crystals might not be sufficiently stable under relevant reaction conditions.

Recently it has been shown that mesopores can be introduced into zeolite crystals e.g. by conducting the hydrothermal crystallisation within a carbon black material U.S. Pat. Nos. 6,620,402 and 6,565,826, and C. J. H. Jacobsen, C. Madsen, J. Houzvicka, I. Schmidt, A. Carlsson, *J. Am. Chem. Soc.* 2000, 122, 7116, all incorporated herein by reference). Controlled combustion of the carbon black template leads to mesoporous zeolite single crystals with mesopores the size of carbon black particles. This reduces the experimental work for the formation of mesopores significantly, but more importantly it dramatically increases the maximally available mesopore volume of the zeolite crystals (C. J. H. Jacobsen, J. Houzvicka, A. Carisson, I. Schmidt, *Stud. Surf. Sci. Catal.* 2001, 135, 167, incorporated herein by reference).

Such mesoporous zeolite crystals with a non-crystallographic mesopore system resulting from the removal of a mesopore template after zeolite crystallisation are useful host materials.

First of all, they possess the (crystallographic) micropore system which is characteristic of the relevant zeolite. They have high specific external surface areas compared to conventional zeolite crystals due to the (non-crystallographic) mesopore system and finally they have crystal sizes that are sufficiently large to allow separation of the crystals by filtration. This makes the mesoporous zeolites a more appropriate support material for immobilised catalytically active metal complexes than other known zeolite materials.

It is therefore an object of the invention to provide a catalytic material comprising an immobilised homogeneous catalyst within zeotype crystals with a non-crystallographic mesopore system and a mesopore volume of the zeotype crystals above 0.25 ml/g.

It is also an object of the invention to provide a process for preparing the catalytic material of the invention.

The homogeneous catalyst is immobilised in zeotype crystals having a non-crystallographic mesopore system and a mesopore volume above 0.25 mug. The mesopores have a diameter from 20–50 Å, and they are introduced into the individual zeolite crystals by removal of a mesopore template incorporated during crystallisation. The mesopore template can be removed by combustion, dissolution, sublimation or melting. The resulting mesopore system is non-crystallographic as it results from the growth of the zeolite material around the template. This process is described in greater detail in U.S. Pat. Nos. 6,620,402 and 6,565,826, as mentioned earlier.

The micropores present in the zeotype represent a crystallographic pore system with each unit cell having a regular lattice showing the position of the individual atoms in the cell. The channels resulting from the positions of the individual atoms relative to one another are determined by the crystallography. The mesopores are not surrounded by miropores, and this is advantageous since the mesopores obtain direct entrance to the surface. This minimises diffusion limitations.

The examples illustrate the immobilisation of the homogeneous catalysts:

Jacobsen's catalyst (N,N'-bis(3,5-di-tert-butyl-salicylidene)-1,2-cyclohexane-diamino-manganese chloride (L. Frunza, H. Kosslick, H. Landmesser, E. Höft, R. Fricke, J. Mol. Catal. A: Chemical 1997, 123, 179)), $CoMn_2$ ($\mu_3$-O) ($MeCO_2$)$_6$(py)$_3$ (S. A. Chavan, D. Srinivas, P. Ratnasamy, Chem. Commun. 2001, 1124).

The metal complex catalysts and the catalytic reactions applied in this disclosure are well known in the literature.

The zeotypes are exemplified by zeolites, and typical MFI-type zeolites that can be used in the process of the invention are ZSM-5, zeolites Y and β. However, the process of the invention is not restricted to these, but can be applied to other zeotypes.

In the process of the invention the homogeneous catalyst can be synthesised from metal ions and suitable ligands or ligand precursors introduced into the mesoporous zeotype sequentially. When metal complexes such as those mentioned above are used, they can contain one or more metal atoms of one or more elements.

The resulting catalytic material obtained by immobilising the homogeneous catalyst in the zeotype crystals is therefore a homogeneous catalyst in a heterogenized form.

The catalytic material of the invention can be used in both continuous and batch processes, where it can be installed in, for example, fixed bed reactors. It can also be used in slurry phase reactions after which the catalytic material can be recovered by filtration. A further advantage is that it can be used in gas phase reactions.

The catalytic material of the invention can be applied in many processes, amongst them alkene epoxidations and pxylene oxidations.

Immobilisation of the homogeneous catalyst in the zeotype can be demonstrated by IR and UV-VIS spectroscopy.

The presence of a crystallographic micropore system can be identified by X-ray diffraction (XRD). The pore volume of the non-crystallographic mesopore system can be determined by eg. Hg intrusion or by the BJH method using the $N_2$ desorption isotherm at 77 K.

COMPARATIVE EXAMPLE 1

2.0 g of conventional, non-mesoporous MFI type zeolite was ion-exchanged with an aqueous solution of 1.0 g $Mn(CH_3COO)_2 \cdot 4H_2O$ at room temperature for 24 h. After filtration and drying the zeolitic material was suspended in $CH_2Cl_2$/methanol (1:1). To this slurry was added 0.10 ml diaminocyclohexane. The mixture was stirred for 24 h. After addition of 200 mg 3,5-di(tert-butyl)salicylaldehyde and 100 mg LiCi, the mixture was stirred in air for another 48 h.

The resulting light brown material, Jacobsen's catalyst immobilised in non-mesoporous MFI type zeolite, was filtered, washed several times with $CH_2Cl_2$ and dried in air at 50° C.

COMPARATIVE EXAMPLE 2

2.0 g of conventional, non-mesoporous MFI type zeolite were ion-exchanged with aqueous solutions of 0.50 g $Co(CH_3COO)_2 \cdot 4H_2O$ and 0.98 g Mn $(CH_3COO)_2 \cdot 4H_2O$ (molar ratio Co:Mn 1:2) at 65° C. for 4 h. After filtration and drying the zeolitic material was suspended in glacial $CH_3COOH$ (18 ml). To this slurry was added pyridine (3.6 ml), NaBr (0.60 g) and $H_2O_2$ (35%, 7.7 ml). This mixture was stirred at RT while a stream of air was passed through the solution for 2 h.

After filtration the product, the catalyst of Chavan et al. immobilised in non-mesoporous MFI type zeolite was washed with $CH_3COOH$ and dried in vacuum.

EXAMPLE 3

2.0 g of mesoporous MFI type zeolite were ion-exchanged with an aqueous solution of 1.0 g $Mn(CH_3COO)_2 \cdot 4H_2O$ at room temperature for 24 h. After filtration and drying the zeolitic material was suspended in $CH_2Cl_2$/methanol (1:1). To this slurry was added 0.10 ml diaminocyclohexane. The mixture was stirred for 24 h. After addition of 200 mg 3,5-di (tbutyl) salicylaldehyde and 100 mg LiCl, the mixture was stirred in air for another 48 h.

The resulting light brown material, Jacobsen's catalyst immobilised in mesoporous MFI type zeolite was filtered, washed several times with $CH_2Cl_2$ and dried in air at 50° C.

EXAMPLE 4

2.0 g of mesoporous MFI type zeolite were ion-exchanged with aqueous solutions of 0.50 g $Co(CH_3COO)_2 \cdot 4H_2O$ and 0.98 g Mn $(CH_3COO)_2 \cdot 4H_2O$ (molar ratio Co:Mn 1:2) at 65° C. for 4 h. After filtration and drying the zeolitic material was suspended in glacial $CH_3COOH$ (18 ml). To this slurry was added pyridine (3.6 ml), NaBr (0.60 g) and $H_2O_2$ (35%, 7.7 ml). This mixture was stirred at RT while a stream of air was passed through the solution for 2 h.

After filtration the product, the catalyst of Chavan et al. immobilised in mesoporous MFI type zeolite was washed with $CH_3COOH$ and dried in vacuum.

The catalyst of Comparative Example 1 had a metal load of 1315 ppm Mn. The catalyst of Example 3 had a metal load of 5970 ppm Mn.

Infrared spectra of both catalysts could not be distinguished from each other and were almost identical to an infrared spectrum of the unsupported Jacobsen's catalyst N,N'-bis (3,5-di-tert-butylsalicylidene)-1,2-cyclohexanediamino-manganese chloride.

The catalyst of Comparative Example 2 had a metal load of 500 ppm Co and 920 ppm Mn.

The catalyst of Example 4 had a metal load of 1750 ppm Co and 2960 ppm Mn.

UV/vis spectra (190–900 nm) of both catalysts could not be distinguished from each other and were almost identical to an UV/Vis spectrum of the unsupported cluster [$CoMn_2$ ($\mu_3$-O) ($MeCO_2$)$_6$ (py)$_3$].

EXAMPLE 5

An aqueous solution of sodium hypochlorite was mixed with a solution of $Na_{2\ HPO4}$ and the pH value was adjusted to 11.3. The catalyst from either comparative Example 1 (908 mg) or from Example 3 (200 mg, representing identical amounts of Mn for both catalysts) was added to the cooled solution (0° C.). Then 10 mmole of styrene dissolved in 10 ml of dichloromethane were added under stirring. The two-phase mixture was stirred at room temperature for a total of 5 h. Every 20 min. the stirring was interrupted and a sample of the separated organic phase was taken, washed with water, dried over $Na_2SO_4$ and analysed by GC-MS. The mesoporous catalyst from Example 3 showed faster conversion of styrene to styrene epoxide than the non-mesoporous catalyst from comparative Example 1.

EXAMPLE 6

To a mixture of 38 ml acetic acid, 5.6 ml water, 86 mg NaBr and 2.0 ml p-xylene was added the catalyst from either comparative Example 2 (1327 mg) or from Example 4 (400 mg, representing identical amounts of metals for both catalysts). After stirring for some minutes, 3.0 ml of the mixture was pipetted in a small glass vial, which was equipped with a teflon stirrer. The vial was put in the autoclave, which was pressurised with 20 bar synthetic air and heated to 195° C. for 4 h, which caused the pressure to rise to ca. 29 bar. Every 20 min the stirring was interrupted and a sample was taken, dissolved in DMF, filtered and analysed by GC-MS. The mesoporous catalyst from Example 4 showed faster conversion of p-xylene to terephthalic acid than the non-mesoporous catalyst from comparative Example 2.

EXAMPLE 7

The catalysts used in the reactions described in Example 5 were isolated by filtration on a G4 filter, washed with methanol and dichloromethane and dried at 110° C. for 4 h. 99% (198 mg) of the catalyst were recovered. The recovered catalysts were reused in a new catalytic experiment, which was according to the procedure described in Example 5. The reused catalysts showed an unchanged activity compared to the fresh catalysts described in Example 5.

EXAMPLE 8

The catalysts used in the reactions described in Example 6 were isolated by filtration on a G4 filter, washed with methanol and dichloromethane and dried at 110° C. for 4 h. 99% (396 mg) of the catalyst were recovered. The recovered catalysts were reused in a new catalytic experiment, which was according to the procedure described in Example 6. The reused catalysts showed an unchanged activity compared to the fresh catalysts described in Example 6.

What is claimed is:

1. Catalytic material comprising an immobilised homogeneous catalyst within zeolite crystals with a non-crystallographic mesopore system and a mesopore volume of the zeolite crystals above 0.25 ml/g obtained by removal of a carbon template incorporated during crystallisation of the individual zeolite crystals.

2. Catalytic material according to claim 1 comprising catalytic material from metal ions and suitable ligands or ligand precursors.

3. Catalytic material according to claim 1 comprising a metal complex consisting of one or more metal atoms of one or more elements.

4. Process for the preparation of catalytic material according to claim 1 comprising immobilizing the homogeneous catalytic material in zeolite crystals with a non-crystallographic mesopore system and a mesopore volume of the zeolite crystals above 0.25 ml/g obtained by removal of a carbon template incorporated during crystallisation of the individual zeolite crystals.

5. Process according to claim 4 comprising immobilizing catalytically active homogeneous metal complexes.

6. Process of claim 4 comprising immobilizing catalytically active homogeneous metal complex precursors introduced into the mesoporous zeolite sequentially.

7. Process of claim 5 comprising immobilizing catalytically active homogeneous metal complex precursors introduced into the mesoporous zeolite sequentially.

* * * * *